(12) United States Patent
Wu et al.

(10) Patent No.: US 10,876,099 B2
(45) Date of Patent: Dec. 29, 2020

(54) PREPARATION AND APPLICATION OF CYCLODEXTRIN GLUCOSYLTRANSFERASE MUTANT

(71) Applicant: Jiangnan University, Wuxi (CN)

(72) Inventors: Jing Wu, Wuxi (CN); Lingqia Su, Wuxi (CN); Xiumei Tao, Wuxi (CN); Yusheng Wang, Wuxi (CN); Junchen Dong, Wuxi (CN)

(73) Assignee: Jiangnan University, Wuxi (CN)

( * ) Notice: Subject to any disclaimer, the term of this patent is extended or adjusted under 35 U.S.C. 154(b) by 140 days.

(21) Appl. No.: 15/991,322

(22) Filed: May 29, 2018

(65) Prior Publication Data
US 2019/0218530 A1    Jul. 18, 2019

(30) Foreign Application Priority Data

Jan. 15, 2018  (CN) .......................... 2018 1 0033878

(51) Int. Cl.
*C12N 9/10*  (2006.01)
*C12P 19/60*  (2006.01)

(52) U.S. Cl.
CPC ............ *C12N 9/1074* (2013.01); *C12P 19/60* (2013.01); *C12Y 204/01019* (2013.01)

(58) Field of Classification Search
CPC .................................................... C12N 9/1074
See application file for complete search history.

(56) References Cited

U.S. PATENT DOCUMENTS 6,004,790 A * 12/1999 Dijkhuizen .......... C12N 9/1074
435/193

* cited by examiner

*Primary Examiner* — Rebecca E Prouty
(74) *Attorney, Agent, or Firm* — IPro, PLLC; Na Xu (57) ABSTRACT

The present invention relates to preparation and application of a cyclodextrin glucosyltransferase mutant, belonging to the fields of gene engineering and enzyme engineering. By mutating amino acids of cyclodextrin glucosyltransferase, the enzyme activity of the obtained mutant can reach 2.5 times that of wild enzyme. In addition, the cyclodextrin glucosyltransferase mutant obtained in the present invention is simple in purification and suitable for industrial production.

4 Claims, 5 Drawing Sheets

Specification includes a Sequence Listing.

SEQUENCE LISTING

```
<160> NUMBER OF SEQ ID NOS: 13

<210> SEQ ID NO 1
<211> LENGTH: 680
<212> TYPE: PRT
<213> ORGANISM: Artificial Sequence
<220> FEATURE:
<223> OTHER INFORMATION: Protein translated from synthetic DNA

<400> SEQUENCE: 1

Ala Gly Asn Leu Asn Lys Val Asn Phe Thr Ser Asp Val Val Tyr Gln
1               5                   10                  15

Ile Val Val Asp Arg Phe Val Asp Gly Asn Thr Ser Asn Asn Pro Ser
            20                  25                  30

Gly Ala Leu Phe Ser Ser Gly Cys Thr Asn Leu Arg Lys Tyr Cys Gly
        35                  40                  45

Gly Asp Trp Gln Gly Ile Ile Asn Lys Ile Asn Asp Gly Tyr Leu Thr
    50                  55                  60
```

-continued

```
Asp Met Gly Val Thr Ala Ile Trp Ile Ser Gln Pro Val Glu Asn Val
 65                  70                  75                  80

Phe Ser Val Met Asn Asp Ala Ser Gly Ser Ala Ser Tyr His Gly Tyr
                 85                  90                  95

Trp Ala Arg Asp Phe Lys Lys Pro Asn Pro Phe Phe Gly Thr Leu Ser
            100                 105                 110

Asp Phe Gln Arg Leu Val Asp Ala Ala His Ala Lys Gly Ile Lys Val
        115                 120                 125

Ile Ile Asp Phe Ala Pro Asn His Thr Ser Pro Ala Ser Glu Thr Asn
130                 135                 140

Pro Ser Tyr Met Glu Asn Gly Arg Leu Tyr Asp Asn Gly Thr Leu Leu
145                 150                 155                 160

Gly Gly Tyr Thr Asn Asp Ala Asn Met Tyr Phe His His Asn Gly Gly
                165                 170                 175

Thr Thr Phe Ser Ser Leu Glu Asp Gly Ile Tyr Arg Asn Leu Phe Asp
            180                 185                 190

Leu Ala Asp Leu Asn His Gln Asn Pro Val Ile Asp Arg Tyr Leu Lys
        195                 200                 205

Asp Ala Val Lys Met Trp Ile Asp Met Gly Ile Asp Gly Ile Arg Met
210                 215                 220

Asp Ala Val Arg His Met Pro Phe Gly Trp Gln Lys Ser Leu Met Asp
225                 230                 235                 240

Glu Ile Asp Asn Tyr Arg Pro Val Phe Thr Phe Gly Glu Trp Phe Leu
                245                 250                 255

Ser Glu Asn Glu Val Asp Ala Asn Asn His Tyr Phe Ala Asn Glu Ser
            260                 265                 270

Gly Met Ser Leu Leu Asp Phe Arg Phe Gly Gln Lys Leu Arg Gln Val
        275                 280                 285

Leu Arg Asn Asn Ser Asp Asn Trp Tyr Gly Phe Asn Gln Met Ile Gln
290                 295                 300

Asp Thr Ala Ser Ala Tyr Asp Glu Val Leu Asp Gln Val Thr Phe Ile
305                 310                 315                 320

Asp Asn His Asp Met Asp Arg Phe Met Ile Asp Gly Gly Asp Pro Arg
                325                 330                 335

Lys Val Asp Met Ala Leu Ala Val Leu Leu Thr Ser Arg Gly Val Pro
            340                 345                 350

Asn Ile Tyr Tyr Gly Thr Glu Gln Tyr Met Thr Gly Asn Gly Asp Pro
        355                 360                 365

Asn Asn Arg Lys Met Met Ser Ser Phe Asn Lys Asn Thr Arg Ala Tyr
370                 375                 380

Gln Val Ile Gln Lys Leu Ser Ser Leu Arg Arg Asn Asn Pro Ala Leu
385                 390                 395                 400

Ala Tyr Gly Asp Thr Glu Gln Arg Trp Ile Asn Gly Asp Val Tyr Val
                405                 410                 415

Tyr Glu Arg Gln Phe Gly Lys Asp Val Val Leu Val Ala Val Asn Arg
            420                 425                 430

Ser Ser Ser Ser Asn Tyr Ser Ile Thr Gly Leu Phe Thr Ala Leu Pro
        435                 440                 445

Ala Gly Thr Tyr Thr Asp Gln Leu Gly Gly Leu Leu Asp Gly Asn Thr
450                 455                 460

Ile Gln Val Gly Ser Asn Gly Ser Val Asn Ala Phe Asp Leu Gly Pro
465                 470                 475                 480
```

-continued

Gly Glu Val Gly Val Trp Ala Tyr Ser Ala Thr Glu Ser Thr Pro Ile
                485                 490                 495

Ile Gly His Val Gly Pro Met Met Gly Gln Val Gly His Gln Val Thr
            500                 505                 510

Ile Asp Gly Glu Gly Phe Gly Thr Asn Thr Gly Thr Val Lys Phe Gly
        515                 520                 525

Thr Thr Ala Ala Asn Val Val Ser Trp Ser Asn Asn Gln Ile Val Val
    530                 535                 540

Ala Val Pro Asn Val Ser Pro Gly Lys Tyr Asn Ile Thr Val Gln Ser
545                 550                 555                 560

Ser Ser Gly Gln Thr Ser Ala Ala Tyr Asp Asn Phe Glu Val Leu Thr
                565                 570                 575

Asn Asp Gln Val Ser Val Arg Phe Val Val Asn Asn Ala Thr Thr Asn
            580                 585                 590

Leu Gly Gln Asn Ile Tyr Ile Val Gly Asn Val Tyr Glu Leu Gly Asn
        595                 600                 605

Trp Asp Thr Ser Lys Ala Ile Gly Pro Met Phe Asn Gln Val Val Tyr
    610                 615                 620

Ser Tyr Pro Thr Trp Tyr Ile Asp Val Ser Val Pro Glu Gly Lys Thr
625                 630                 635                 640

Ile Glu Phe Lys Phe Ile Lys Lys Asp Ser Gln Gly Asn Val Thr Trp
                645                 650                 655

Glu Ser Gly Ser Asn His Val Tyr Thr Thr Pro Thr Asn Thr Thr Gly
            660                 665                 670

Lys Ile Ile Val Asp Trp Gln Asn
        675                 680

<210> SEQ ID NO 2
<211> LENGTH: 27
<212> TYPE: DNA
<213> ORGANISM: Artificial Sequence
<220> FEATURE:
<223> OTHER INFORMATION: Synthetic DNA

<400> SEQUENCE: 2
gcggcgcatg ctgaaggtat taaggtg                                      27

<210> SEQ ID NO 3
<211> LENGTH: 27
<212> TYPE: DNA
<213> ORGANISM: Artificial Sequence
<220> FEATURE:
<223> OTHER INFORMATION: Synthetic DNA

<400> SEQUENCE: 3
caccttaata ccttcagcat gcgccgc                                      27

<210> SEQ ID NO 4
<211> LENGTH: 35
<212> TYPE: DNA
<213> ORGANISM: Artificial Sequence
<220> FEATURE:
<223> OTHER INFORMATION: Synthetic DNA

<400> SEQUENCE: 4
tgtttaccgc gctgccggct agcacctaca ccgat                             35

<210> SEQ ID NO 5
<211> LENGTH: 35
<212> TYPE: DNA

```
<213> ORGANISM: Artificial Sequence
<220> FEATURE:
<223> OTHER INFORMATION: Synthetic DNA

<400> SEQUENCE: 5
atcggtgtag gtgctagccg gcagcgcggt aaaca                                35

<210> SEQ ID NO 6
<211> LENGTH: 27
<212> TYPE: DNA
<213> ORGANISM: Artificial Sequence
<220> FEATURE:
<223> OTHER INFORMATION: Synthetic DNA

<400> SEQUENCE: 6
ctggacggta acacctttca ggttggc                                         27

<210> SEQ ID NO 7
<211> LENGTH: 27
<212> TYPE: DNA
<213> ORGANISM: Artificial Sequence
<220> FEATURE:
<223> OTHER INFORMATION: Synthetic DNA

<400> SEQUENCE: 7
gccaacctga aggtgttac cgtccag                                          27

<210> SEQ ID NO 8
<211> LENGTH: 31
<212> TYPE: DNA
<213> ORGANISM: Artificial Sequence
<220> FEATURE:
<223> OTHER INFORMATION: Synthetic DNA

<400> SEQUENCE: 8
gccggagggt aaaactaccg agtttaaatt c                                    31

<210> SEQ ID NO 9
<211> LENGTH: 31
<212> TYPE: DNA
<213> ORGANISM: Artificial Sequence
<220> FEATURE:
<223> OTHER INFORMATION: Synthetic DNA

<400> SEQUENCE: 9
gaatttaaac tcggtagttt taccctccgg c                                    31

<210> SEQ ID NO 10
<211> LENGTH: 34
<212> TYPE: DNA
<213> ORGANISM: Artificial Sequence
<220> FEATURE:
<223> OTHER INFORMATION: Synthetic DNA

<400> SEQUENCE: 10
cgagtttaaa ttcatcgaaa aagactctca gggc                                 34

<210> SEQ ID NO 11
<211> LENGTH: 34
<212> TYPE: DNA
<213> ORGANISM: Artificial Sequence
<220> FEATURE:
<223> OTHER INFORMATION: Synthetic DNA

<400> SEQUENCE: 11
gccctgagag tcttttcga tgaatttaaa ctcg                                  34
```

```
<210> SEQ ID NO 12
<211> LENGTH: 29
<212> TYPE: DNA
<213> ORGANISM: Artificial Sequence
<220> FEATURE:
<223> OTHER INFORMATION: Synthetic DNA

<400> SEQUENCE: 12
cccgacttgg tataccgatg tttctgtgc                                29

<210> SEQ ID NO 13
<211> LENGTH: 29
<212> TYPE: DNA
<213> ORGANISM: Artificial Sequence
<220> FEATURE:
<223> OTHER INFORMATION: Synthetic DNA

<400> SEQUENCE: 13
gcacagaaac atcggtatac caagtcggg                                29
```

PREPARATION AND APPLICATION OF CYCLODEXTRIN GLUCOSYLTRANSFERASE MUTANT

TECHNICAL FIELD

The present invention relates to preparation and application of a cyclodextrin glucosyltransferase mutant, belonging to the fields of gene engineering and enzyme engineering.

BACKGROUND

Vitamin C (VC) is a water-soluble vitamin that the human body cannot synthesize by itself, and participates in many physiological activities in the body, such as promoting the conversion of cholesterol to bile acid, promoting the synthesis of adrenal cortical hormone, participating in the metabolism of aromatic amino acid, promoting iron absorption, and participating in a variety of redox reactions in the body, thereby playing an important role in maintaining and promoting human health. In addition, the vitamin C can also promote the synthesis of collagen and reduce melanin that has been formed, and has a certain effect on maintaining skin elasticity, whitening, and removing wrinkles. The vitamin C is widely used in the fields of food, medicines, cosmetics and the like. However, the hydroxy of the 2-position carbon of the VC is extremely unstable, and can be oxidatively degraded very easily, which limits its application. 2-O-α-D-glucopyranosyl-ascorbic acid (AA-2G) is a saccharide derivative of the vitamin C, is the most stable and best-performing alternative to the VC, and has been mainly used as a whitening additive for many brands of high-end cosmetics in recent years.

Currently, the AA-2G is mainly generated through biological catalysis of glycosyltransferases among which cyclodextrin glucosyltransferase is the most commonly used catalytic enzyme. In the prior art, there are many studies on the genetic modification and high-level expression of the cyclodextrin glucosyltransferase, but many problems still occur in the realization of industrial production of the cyclodextrin glucosyltransferase, such as low enzyme yield, low conversion rate in catalytic preparation of the AA-2G and the like. Therefore, the use of gene engineering and enzyme engineering means to increase the yield of the cyclodextrin glucosyltransferase will be more conducive to industrial production.

SUMMARY

The present invention firstly aims to provide a cyclodextrin glucosyltransferase mutant, which comprises substitution of one or two active amino acid residues relative to cyclodextrin glucosyltransferase of which an amino acid sequence is as shown in SEQ ID NO.1.

In an implementation of the present invention, the mutant has mutation of one or two amino acid sites relative to the cyclodextrin glucosyltransferase of which the amino acid sequence is as shown in SEQ ID NO.1.

In an implementation of the present invention, the yield of the mutant is increased to some extent.

In an implementation of the present invention, the mutant results from mutation of one or two sites from lysine (Lys) at the 124 position, glycine (Gly) at the 450 position, isoleucine (Ile) at the 465 position, isoleucine (Ile) at the 641 position, lysine (Lys) at the 647 position or isoleucine (Ile) at the 631 position of cyclodextrin glucosyltransferase of which an amino acid sequence is as shown in SEQ NO.1.

In an implementation of the present invention, the mutant results from mutation of lysine (Lys) at the 124 position of the cyclodextrin glucosyltransferase of which the amino acid sequence is as shown in SEQ ID NO.1 to glutamic acid (Glu), herein the mutant is named K124E.

In an implementation of the present invention, the mutant results from mutation of glycine (Gly) at the 450 position of the cyclodextrin glucosyltransferase of which the amino acid sequence is as shown in SEQ ID NO.1 to serine (Ser), wherein the mutant is named. G450S.

In an implementation of the present invention, the mutant results from mutation of isoleucine (Ile) at the 465 position of the cyclodextrin glucosyltransferase of which the amino acid sequence is as shown in SEQ ID NO.1 to phenylalanine (Phe), wherein the mutant is named I465F.

In an implementation of the present invention, the mutant results from mutation of isoleucine (Ile) at the 641 position of the cyclodextrin glucosyltransferase of which the amino acid sequence is as shown in SEQ ID NO.1 to threonine (Thr), wherein the mutant is named I641T.

In an implementation of the present invention, the mutant results from mutation of lysine (Lys) at the 647 position of the cyclodextrin glucosyltransferase of which the amino acid sequence is as shown in SEQ ID NO.1 to glutamic acid (Glu), wherein the mutant is named K647E.

In an implementation of the present invention, the mutant results from mutation of isoleucine (Ile) at the 631 position of the cyclodextrin glucosyltransferase of which the amino acid sequence is as shown in SEQ ID NO.1 to threonine (Thr), wherein the mutant is named I631T.

In an implementation of the present invention, the mutant results from mutation of isoleucine (Ile) at the 641 position of the cyclodextrin glucosyltransferase of which the amino acid sequence is as shown in SEQ ID NO.1 to threonine (Thr) and lysine (Lys) at the 647th position to glutamic acid (Glu) at the same time, wherein the mutant is named I641T/K647E.

In an implementation of the present invention, the mutant results from mutation of isoleucine (Ile) at the 641 position of the cyclodextrin glucosyltransferase of which the amino acid sequence is as shown in SEQ ID NO.1 to threonine (Thr) and isoleucine (Ile) at the 631st position to threonine (Thr) at the same time, wherein the mutant is named I641T/I631T.

In an implementation of the present invention, the mutant results from mutation of lysine (Lys) at the 647 position of the cyclodextrin glucosyltransferase of which the amino acid sequence is as shown in SEQ ID NO.1 to glutamic acid (Glu) and isoleucine (Ile) at the 631 position to threonine (Thr) at the same time, herein the mutant is named K647E/I631T.

The present invention secondly aims to provide a preparation method of the cyclodextrin glucosyltransferase mutant, which comprises the following steps:

(1) according to determined mutant sites, designing mutagenic primers of site-directed mutagenesis, and performing site-directed mutagenesis by using a vector carrying a cyclodextrin glucosyltransferase gene as a template; and constructing a plasmid vector containing the gene coding the mutant;

(2) transforming a mutant plasmid into a host cell; and (3) selecting a positive clone, performing fermentation culture, and performing centrifuging, wherein supernate is a crude enzyme solution of the cyclodextrin glucosyltransferase mutant.

In an implementation of the present invention, the plasmid vector is any of pUC series, pET series or pGEX.

In an implementation of the present invention, the host cell is a bacterial or fungal cell.

In an implementation of the present invention, the bacteria are Gram-negative bacteria or Gram-positive bacteria.

The present invention has the following beneficial effects:

The present invention provides a cyclodextrin glucosyltransferase mutant with improved yield. The enzyme activity of the mutants I641T, K647E, I631T, I641T/K647E, I641T/I631T and K647E/I631T is respectively 2.5 times, 2.4 times, 1.7 times, 1.4 times, 1.6 times and 2 times that of the cyclodextrin glucosyltransferase of which the amino acid sequence is as shown in SEQ ID NO.1. The mutant has the advantages of high yield and simple purification, and is suitable for industrial production.

BRIEF DESCRIPTION OF FIGURES

FIG. 1 SDS-PAGE electrophoretogram
FIG. 2. Optimum temperature of mutant I641T
FIG. 3 Temperature stability of mutant I641T
FIG. 4 Optimum pH of mutant I641T
FIG. 5 pH stability of mutant I641T

DETAILED DESCRIPTION

LB medium: tryptone 10 g·L$^{-1}$, yeast powder 5 g·L$^{-1}$, and sodium chloride 10 g·L$^{-1}$ TB medium: tryptone 12 g·L$^{-1}$, yeast powder 24 g·L$^{-1}$, glycerol 5 g·L$^{-1}$, KH$_2$PO$_4$ 2.31 g·L$^{-1}$, K$_2$HPO$_4$·3H$_2$O 16.43 g·L$^{-1}$, and glycine 7.5 g·L$^{-1}$ Definition of enzyme activity: α-cyclization activity is measured by colorimetry by using properties of α-CD embedded methyl orange. One enzyme activity unit (U) is defined as the amount of enzyme required by generating 1 μmol of α-CD within 1 min under such conditions.

Activity measurement steps:

(1) preheating: taking 2 mL of previously prepared 1% maltodextrin DE 9-13 (50 mM, prepared from a pH5.5 phosphate buffer, and holding at the temperature of 50° C. for 10 min;

(2) reaction: adding 0.1 mL of properly diluted enzyme solution, performing a reaction for 10 min, adding 0.2 mL of 3M HCl to terminate the reaction, and adding 0.2 mL of 0.44 mmol·L$^{-1}$ methyl orange solution; and (3) measurement: holding the above reaction solution at the temperature of 16° C. for 15 min, measuring absorbance at 505 nm and calculating enzyme activity.

Embodiment 1: Preparation of Cyclodextrin Glucosyltransferase Mutant (1) Preparation of mutants According to a gene sequence of the cyclodextrin glucosyltransferase of which the amino acid sequence is as shown in SEQ ID NO.1, primers for introducing K124E, G450S, I465F, I641T, K647E and I631T mutations are respectively designed and synthesized, a cyclodextrin glucosyltransferase gene is subjected to site-directed mutagenesis, a DNA coding sequence is determined, a codon of Lys at the 124 position is converted into a codon of Glu, a codon of Gly at the 450 position is mutated into a codon of Ser, a codon of Ile at the 465 position is mutated into a codon of Phe, a codon of Ile at the 641 position is converted into a codon of Thr, a codon of Lys at the 647 position is converted into a codon of Glu, and a codon of Lys at the 631 position is converted into a codon of Thr. The mutant gene is put into a proper expression vector and led into *Escherichia coli* to be expressed, so as to obtain the cyclodextrin glucosyltransferase.

Site-directed mutagenesis of mutants K124E, G450S, I465F, I641T, K647E and I631T: A rapid PCR technique is utilized, and an expression vector cgt/pET20b(+) is used as a template.

Site-directed mutagenesis primers for introducing K124E mutation are:

```
Forward primer:
5'-GCGGCGCATGCTGAAGGTATTCAAGGTG-3'
(mutated bases are underlined)

Reverse primer:
5'-CACCTTAATACCTTCAGCATGCGCCGC-3'
(mutated bases are underlined)
```

Site-directed mutagenesis primers for introducing G450S mutation are:

```
Forward primer:
5'-TGTTTACCGCGCTGCCGGCTAGCACCTACACCGAT-3'
(mutated bases are underlined)

Reverse primer:
5'-ATCGGTGTAGGTGCTAGCCGGCAGCGCGGTAAACA-3'
(mutated bases are underlined)
```

Site-directed mutagenesis primers for introducing I465F mutation are:

```
Forward primer:
5'-CTGGACGGTAACACCTTTCAGGTTGGC-3'
(mutated bases are underlined)

Reverse primer:
5'-GCCAACCTGAAAGGTGTTACCGTCCAG-3'
(mutated bases are underlined)
```

Site-directed mutagenesis primers for introducing I641T mutation are:

```
Forward primer:
5'-GCCGGAGGGTAAAACTACCGAGTTTAAATTC-3'
(mutated bases are underlined)

Reverse primer:
5'-GAATTTAAACTCGGTAGTTTTACCCTCCGGC-3'
(mutated bases are underlined)
```

Site-directed mutagenesis primers for introducing K647:E mutation are:

```
Forward primer:
5'-CGAGTTTAAATTCATCGAAAAAGACTCTCAGGGC-3'
(mutated bases are underlined)

Reverse primer:
5'-GCCCTGAGAGTCTTTTTCGATGAATTTAAACTCG-3'
(mutated bases are underlined)
```

Site-directed mutagenesis primers for introducing I631T mutation are:

```
Forward primer:
5'-CCCGACTTGGTATACCGATGTTTCTGTGC-3'
(mutated bases are underlined)
```

-continued

```
Reverse primer:
5'-GCACAGAAACATCGGTATACCAAGTCGGG-3'
(mutated bases are underlined)
```

A PCR reaction system is respectively composed of: 5×PS buffer 10 μL, dNTPs Mix (2.5 mM) 4 μL, forward primer (10 μM) 1 μL, reverse primer (10 μM) 1 μL, template DNA 1 μL, PrimeStar HS (5 U/μL) 0.5 μL and double distilled water added to 50 μL.

PCR amplification conditions: performing initial denaturation at 94° C. for 4 min, and performing 25 cycles (98° C. 10 s, 55° C. 5 s and 72° C. 8 min); and continuing extension at 72° C. for 10 min.

(2) Preparation of mutant strains

A PCR product is subjected to DpnI digestion, and transformed into an *Escherichia coli* JM109 competent cell; after the competent cell is cultured in an LB solid medium (containing 100 μg/mL ampicillin) over night, a monoclone is picked and cultured in an LB liquid medium (containing 100 μg/mL ampicillin) and is subjected to plasmid extraction, mutated plasmids are transformed to express the host *Escherichia coli* BL21 (DE3) competent cell, and the sequencing of all the mutated plasmids is proved correct. The recombinant bacteria are named BL21 (DE3)/pET20b (+)-K124E, BL21(DE3)/PEt20b(+)-G450S, BL21(DE3)/cgt/pET20b(+)-I465F, BL21(DE3)/pET20b(+)-I641T, BL21 (DE3)/pET20b(+)-K647E and BL21(DE3)/pET20b(+)-K147E and BL21(DE3)/pET20b(+)-I631T.

Embodiment 2: Single-Mutation Cyclodextrin Glucosyltransferase Activity and Solubility Expression Analysis (1) Expression of mutant enzymes A positive clone transformed into the expression host *Escherichia coli* BL21 (DE3) is picked and grows in an LB liquid medium (containing 100 μg/mL ampicillin) for 8-10 h, a seed fermentation solution is inoculated into a TB culture medium (containing 100 μg/mL ampicillin) according to the inoculum size of 5%, culture is performed in a 25° C. shaking table for 60 h, then a fermentation solution is centrifuged at the speed of 8000 rpm at 4° C. for 10 min to remove thalli, and centrifugal supernate is collected. A supernate obtained by wild cgt/pET20b(±)/*E. coli* BL21 (DE3) fermentation is used as a wild enzyme control.

The enzyme activities of the wild type cyclodextrin glucosyltransferase and the mutant enzymes after 60 h of shake culture are listed in a table, and I641T and K647E have the most obvious effects and have the enzyme activities which are respectively 2.5 times and 2.4 times the enzyme activity of the wild enzyme.

TABLE 1

Enzyme activities of wild cyclodextrin glucosyltransferase and mutants thereof

| Enzyme | Wild Enzyme | I641T | K647E | I631T | K124E | G450S | I465F |
|---|---|---|---|---|---|---|---|
| Enzyme Activity/U · mL$^{-1}$ | 50 | 125 | 120 | 86 | 42 | 50 | 43 |

(3) Solubility expression analysis

Figure 1:
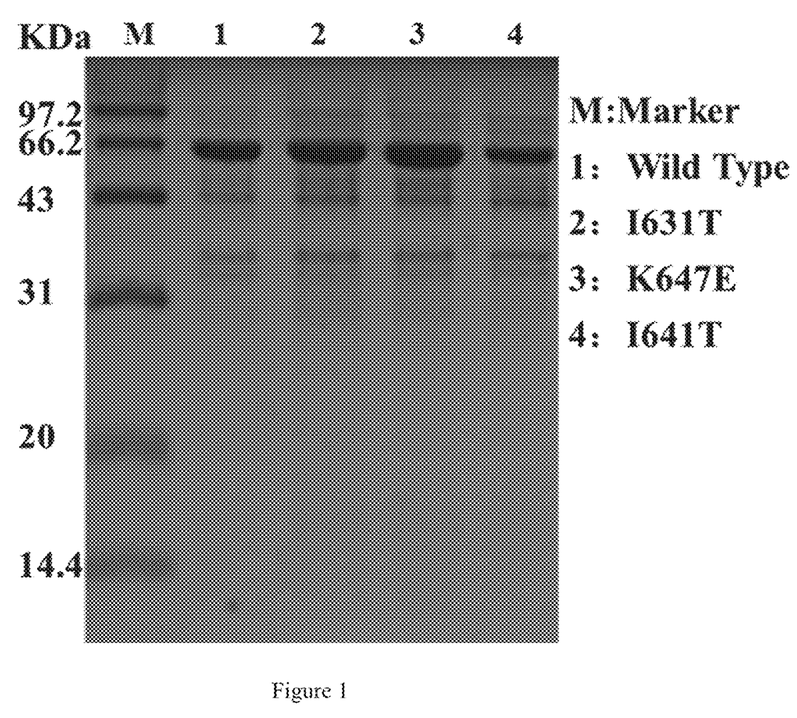

The mutant is centrifuged by a bacterium solution with the same bacterial concentration, 1 mL of 50 mM phosphate buffer is utilized to suspend precipitate, and ultrasonic crushing (the ultrasonic power is 400 W) is performed in an ice bath 80 times (2 s each time) at an interval of 3 s; and the crushed precipitate is subjected to SDS-PAGE electrophoresis analysis. In the SDS-PAGE, a 12% resolving gel and a 4% stacking gel are adopted, and Coomassie brilliant blue R250 is used for staining. The size of the cyclodextrin glucosyltransferase as shown in SDS-PAGE (FIG. 1) is 66 kDa; and the results show that a wall-broken precipitate band of the mutant I641T is lighter than that of the wild enzyme, which indicates that the inclusion body of the mutant I641T is reduced.

Embodiment 3: Preparation and Expression of Cyclodextrin Glucosyltransferase Double-Mutants (1) Preparation of mutants The above three sites are subjected to mutation combination to design double mutations, so as to respectively obtain mutants I641T/K647E, I641T/I631T and I631T/K647E. A preparation method of double-mutant enzymes is that by respectively using I641T, I631T and K647E gene sequences of single-mutant enzymes as templates, primers for introducing double mutations are respectively designed and synthesized, sequence determination is performed, and a mutant gene is put in a proper expression vector and led into *Escherichia coli* to be expressed, thereby obtaining the cyclodextrin glucosyltransferase. Site-directed mutagenesis of mutants I641T/K647E, I641T/I631T and I631T/K647E: a rapid PCR technique is utilized, and an expression vector cgt/pET20b(+) is used as a template.

Site-directed mutagenesis primers for introducing K647E mutation are:

```
Forward primer:
5'-CGAGTTTAAATTCATCGAAAAAGACTCTCAGGGC-3'
(mutated bases are underlined)

Reverse primer:
5'-GCCCTGAGAGTCTTTTTCGATGAATTTAAACTCG-3'
(mutated bases are underlined)
```

Site-directed mutagenesis primers for introducing I641T mutation are:

```
Forward primer:
5'-GCCGGAGGGTAAAACTACCGAGTTTAAATTC-3'
(mutated bases are underlined)

Reverse primer:
5'-GAATTTAAACTCGGTAGTTTTACCCTCCGGC-3'
(mutated bases are underlined)
```

Site-directed mutagenesis primers for introducing I631T mutation are:

```
Forward primer:
5'-CCCGACTTGGTATACCGATGTTTCTGTGC-3'
(mutated bases are underlined)
```

-continued

```
Reverse primer:
5'-GCACAGAAACATCGGTATACCAAGTCGGG-3'
(mutated bases are underlined)
```

A PCR reaction system is respectively composed of: 5×PS buffer 10 μL, dNTPs Mix (2.5 mM) 4 μL, forward primer (10 μM) 1 μL, reverse primer (10 μM) 1 μL, template DNA 1 μL, PrimerStar HS (5 U/μL) 0.5 μL and double distilled water added to 50 μL, PCR amplification conditions: performing initial denaturation at 94° C. for 4 min, and performing 25 cycles (98° C. 10 s, 55° C. 5 s and 72° C. 8 min); and continuing extension at 72° C. for 10 min.

(2) Construction of recombinant strains

A PCR product is subjected to DpnI digestion, and transformed into an *Escherichia coli* JM109 competent cell; after the competent cell is cultured in an LB solid medium (containing 100 μg/mL ampicillin) over night, a monoclone is picked and cultured in an LB liquid medium (containing 100 μg/mL ampicillin) and is subjected to plasmid extraction, the mutated plasmids are transformed to express the host *Escherichia coli* BL21 (DE3) competent cell, and the sequencing of all the mutated plasmids is proved correct. The recombinant bacteria are named BL21(DE3)/pET20b (+)-I641T/K647E, BL21(DE/pET20b(+)-I641T/I163T and BL2 (DE3)/pET20b(+)-I631T/K647E.

(3) Expression of mutant enzymes

A positive clone transformed into the expression host *Escherichia coli* BL21 (DE3) is picked and grows in an LB liquid medium (containing 100 μg/mL ampicillin) for 8-10 h, a seed fermentation solution is inoculated into a TB culture medium (containing 100 μg/mL ampicillin) according to the inoculum size of 5%, culture is performed in a 25° C. shaking table for 60 h, a fermentation solution is centrifuged at the speed of 8000 rpm at 4° C. for 10 min to remove thalli, and centrifugal supernate is collected. A supernate obtained by single-mutation fermentation is used as a wild enzyme control.

(4) Mutant enzyme activity measurement

After the enzyme activities of double mutants I641T/K647E, I641T/I631T and I631T/K647E are measured, the enzyme activities of the cyclodextrin glucosyltransferase wild enzyme, single mutant enzymes and double mutant enzymes after 60 h of shake culture are listed in Table 2, wherein the single mutant and double mutant enzymes have higher enzyme activities to some extent than the wild enzyme.

TABLE 2

Enzyme activities of cyclodextrin glucosyltransferase mutants

| Enzyme | Wild Enzyme | I641T | K647E | I631T | I641T/K647E | I641T/I631T | I631T/K647E |
|---|---|---|---|---|---|---|---|
| Enzyme Activity/U · mL⁻¹ | 50 | 125 | 120 | 86 | 72 | 80 | 100 |

Embodiment 4: Concentrations of Mutant Crude Enzyme Solutions

Ammonium sulfate of which the concentration is 26% relative to the mass of the enzyme solution is added into the enzyme solutions obtained in the embodiment 2 and the embodiment 3 while stirring, stirring is performed until the ammonium sulfate is dissolved, and standing is performed at 4° C. for 8-10 h to precipitate proteins. The mixture is centrifuged (8000 rpm, 10 min) to collect precipitate, a 50 mM KH2PO4-Na2HPO4 buffer (pH 6.0) with the minimum volume is used for redissolution, centrifuging is performed again to remove solids, and supernate is collected and dialyzed to obtain a concentrated enzyme solution.

The enzyme activities of the concentrated enzyme solutions are as follows: wild bacterium 350 U/mL, I641T 900 U/mL, K647E 700 U/mL, I631T 550 U/mL, I641T/K647E 500 U/mL, I641T/I631T 500 U/mL and I631T/K647E 600 U/mL.

Embodiment 5: HPLC Detection of Yield of 2-O-α-D-Glucopyranosyl-Ascorbic Acid 50 g/L L-ascorbic acid and 50 g/L liquefied potato starch (a DE value is about 5) are added as a substrate into a reactor, pH is regulated to 5.0 by using a 20% sodium hydroxide water solution, the enzyme activity of a concentrated enzyme solution of the wild enzyme and the mutant enzymes is regulated to 300 U/mL, 250 U of the wild enzyme and the mutant enzymes is respectively added, and a reaction is performed in a 35° C. 150 rpm shaking water bath for 24 h; after the reaction is finished, 60 U of glucoamylase is added, a reaction is performed in a 60° C. 150 rpm shaking water bath for 24 h, a sample is taken, and a trichloroacetic acid solution (10%, v/v) with the same volume is added to terminate the reaction and precipitate proteins; and after the precipitation is performed for 4 h, the sample is centrifuged at the speed of 12000 rpm for 10 min, supernate is properly diluted and filtered through a 0.45 μm ultrafiltration membrane, and HPLC analysis is performed. Chromatographic conditions are as follows: Agilent 1200HPLC chromatograph, Agilent automatic sampler, Agilent SB-Aq 5 μm(4.6 mm×250 mm), and LC-9A ultraviolet detector; a mobile phase is 20 mM dilute phosphoric acid, and a flow rate is 0.8 mL min⁻¹; and column temperature is 35° C.

The AA-2G yields of the wild enzyme and the mutants are as shown in Table 3; the AA-2G yield of the mutants is about 33.5 g/L, and the yield of the wild enzyme is 33.01 g/L; and the mutants I641 T, K647E, I163 T, I641T/K647E, I641T/I631T and I631T/K647E do not affect the synthesis of AA-2G by enzymatic transformation.

TABLE 3

AA-2G yields of wild cyclodextrin glucosyltransferase and mutants

| Enzyme | Wild Enzyme | I641T | K647E | I631T | I641T/ K647E | I641T/ I631T | I631T/ K647E |
|---|---|---|---|---|---|---|---|
| AA-2G Yield (g/L) | 33.01 | 33.86 | 33.02 | 33.56 | 33.1 | 33.65 | 33.84 |

Embodiment 6: Yields of Mutant Enzymes by Fermentation in Fermentation Tank

Seed activation: the wild bacterium and the recombinant bacterium BL21(DE3)/pET20b(+)-I641T are respectively inoculated into an LB solid medium containing 100 μg·m $L^{-1}$ Amp antibiotics, are put in a 37° C. thermostatic incubator and are cultured for 10-12 h, and a single colony is picked and inoculated into an LB liquid medium containing 100 μg·m $L^{-1}$ Amp antibiotics and is cultured at 37° C. at the speed of 200r·min$^{-1}$ for 8-10 h.

Seed culture: 100 μL of bacterium solution is sucked from the activated bacterium solution in the previous step and is inoculated into 50 mL of seed culture medium, and culture is performed at 37° C. at the speed of 200 r·min-1 for 8-10 h.

3L fermentation tank culture: in this experiment, an infors 3.61 L full-automatic fermentation tank is adopted, and the initial loaded liquid volume is 1.2 L. The seed solution obtained in the previous step is inoculated into the fermentation tank according to the inoculum size of 8%, and in the meanwhile, 100 μg·m $L^{-1}$ Amp antibiotics are added, wherein initial dissolved oxygen in the tank is set as 100%, and initial speed is 300 r·min$^{-1}$; a pH value is set as 7.0; after a seed is inoculated, the initial dissolved oxygen in the tank and the speed are set to be coupled so as to control the dissolved oxygen in the tank at about 30%; and 7-8 h after the inoculation, a carbon source is exhausted, the dissolved oxygen rebounds, and at this time, exponential feeding is performed on a fed-batch liquid at the specific growth rate μ=0.2 h$^{-1}$ for feeding. A sample is taken every 4 h. In the whole fermentation process, 25% ammonia water is fed to regulate the pH to keep the pH in the tank at about 7.0 all the time; when OD600 reaches 15, glycine is replenished, wherein the final concentration of the glycine is 10 g·L$^{-1}$; and when OD600 reaches 50, lactose is fed to the I641T mutant at the flow rate of 0.3 g·L$^{-1}$·h$^{-1}$ to perform induction, wherein the induction temperature is 32° C. Lactose is fed to the wild bacterium at the flow rate of 0.2 g·L$^{-1}$·h$^{-1}$ to perform induction, wherein the induction temperature is 32° C.

After the fermentation is finished, supernate is subjected to extraction to obtain a crude enzyme solution. The enzyme activities of the wild enzyme and the mutant I641T are respectively 290 U/mL and 750 U/mL, which indicates that the enzyme activity of the mutant I641T is much higher than that of the wild enzyme.

Figure 2:
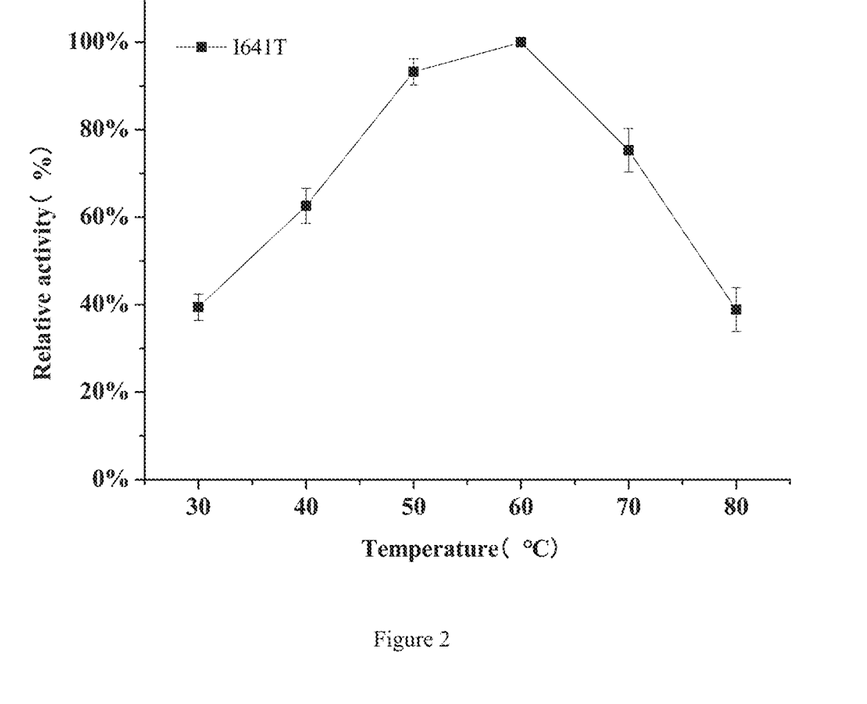
Figure 3:
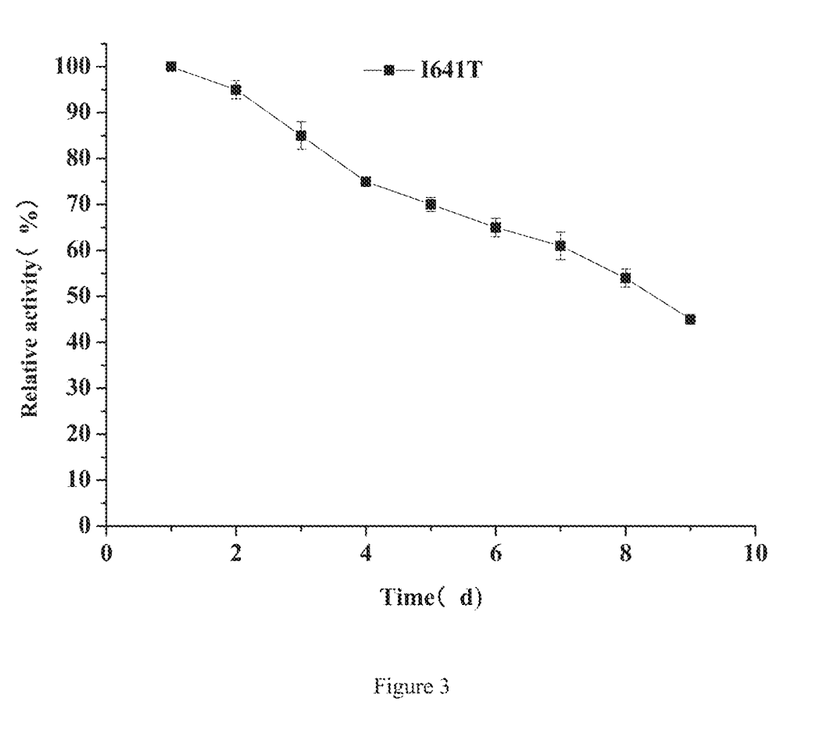

Embodiment 7: Measurement of Enzymatic Properties (1) Optimum temperature and temperature stability By using DE 9-13 maltodextrin as a substrate (pH 5.5), CGTase enzyme activity is measured every 10° C. within the range of 30-80° C.; and by defining the maximum enzyme activity as 100%, the relative enzyme activity at various temperatures is calculated to determine the optimum temperature of the enzyme. Measurement of heat stability of enzyme is that the enzyme is periodically sampled at 40° C. to measure the residual enzyme activity of the enzyme (the initial enzyme activity is defined as 100%), and the change of the enzyme activity of the mutant I641T along with the temperature is as shown in FIG. 2, which indicates that the optimum temperature of the enzyme activity of the mutant is 50° C. The temperature stability of the mutant I641T is as shown in FIG. 3, wherein the half life at 40° C. is 9 d.

(2) Optimum pH and pH stability

Figure 4:
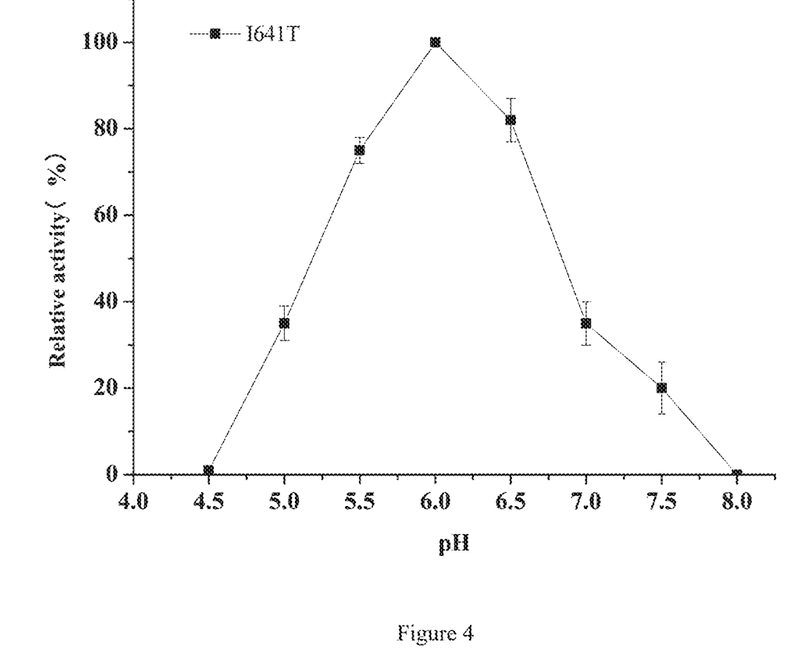
Figure 5:
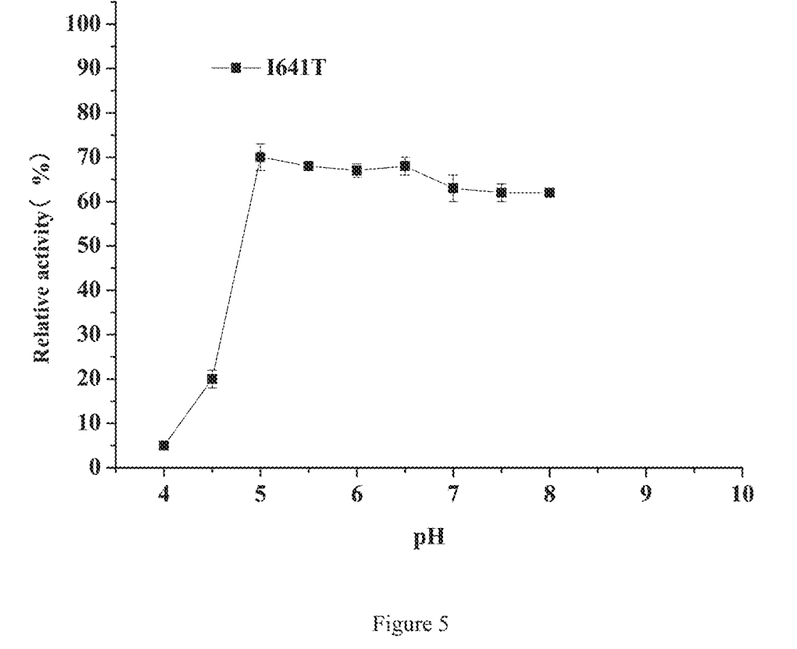

A substrate DE 9-13 maltodextrin with different pH is prepared by using a citric acid-disodium hydrogen phosphate buffer with different pH, and the enzyme activity is measured at 50° C. at an interval of 0.5 unit within the range of pH4.0-8.0; and by defining the maximum enzyme activity as 100% the relative enzyme activity of the mutant enzyme under various other pH conditions is calculated to determine the optimum pH of the mutantenzyme. The mutant enzyme is put in the pH buffer at 4° C., a sample is periodically taken to measure the residual enzyme activity (the initial enzyme activity is 100%), and the change of the enzyme activity of the mutant I641T along with pH is as shown in FIG. 4, which indicates that the optimum pH of the enzyme activity of the mutant is 6.0. The pH stability of the mutant I641T is as shown in FIG. 5, wherein after 10 days within the range of pH5.0-8.0, the residual enzyme activity is still 60% or above, and the enzyme has poor stability under the condition of pH5.0 or below.

It can be seen that the mutant I641T has relatively stable enzymatic properties and is suitable for industrial production.

What is claimed is:

1. A cyclodextrin glucosyltransferase mutant, wherein the cyclodextrin glucosyltransferase mutant has the amino acid sequence SEQ ID NO:1
except for one or more mutations selected from the group consisting of
K124E, G450S, I465F, I641T, K647E, I631T, double mutant I641T and K647E, and double mutant I641T and I631T.

2. A method of constructing a recombinant bacterium expressing the mutant of claim 1, comprising the following steps:
designing mutagenic primers of site-directed mutagenesis,
performing site-directed mutagenesis by using a vector comprising a gene encoding a parent cyclodextrin glucosyltransferase of SEQ ID NO:1 as a template to generate a gene encoding the mutant of claim 1;
constructing a plasmid vector containing the gene encoding the mutant of claim 1;
transforming the vector into a host cell;
selecting a positive clone,
culturing the positive clone, and
centrifuging the culture to generate a supernatant, wherein the supernatant is a crude enzyme solution of the cyclodextrin glucosyltransferase mutant of claim 1.

3. The method of claim 2, wherein the vector is a pUC, pET, or pGEX vector.

4. The method of claim 2, wherein the host cell is a bacterial or fungal cell.

* * * * *